(12) United States Patent
Utiramerur et al.

(10) Patent No.: US 11,566,281 B2
(45) Date of Patent: Jan. 31, 2023

(54) SYSTEMS AND METHODS FOR PAIRED END SEQUENCING

(71) Applicant: LIFE TECHNOLOGIES CORPORATION, Carlsbad, CA (US)

(72) Inventors: Sowmi Utiramerur, Pleasanton, CA (US); Simon Cawley, Oakland, CA (US); Yongming Sun, San Ramon, CA (US); Fiona Hyland, San Mateo, CA (US)

(73) Assignee: Life Technologies Corporation, Carlsbad, CA (US)

( * ) Notice: Subject to any disclaimer, the term of this patent is extended or adjusted under 35 U.S.C. 154(b) by 52 days.

(21) Appl. No.: 16/145,373

(22) Filed: Sep. 28, 2018

(65) Prior Publication Data
US 2019/0100797 A1     Apr. 4, 2019

Related U.S. Application Data

(62) Division of application No. 13/787,221, filed on Mar. 6, 2013, now abandoned.

(60) Provisional application No. 61/640,288, filed on Apr. 30, 2012.

(51) Int. Cl.
| | |
|---|---|
| *C12Q 1/6869* | (2018.01) |
| *G16B 30/00* | (2019.01) |
| *G16B 30/10* | (2019.01) |

(52) U.S. Cl.
CPC ......... *C12Q 1/6869* (2013.01); *G16B 30/00* (2019.02); *G16B 30/10* (2019.02)

(58) Field of Classification Search
None
See application file for complete search history.

(56) References Cited

U.S. PATENT DOCUMENTS

| | | | |
|---|---|---|---|
| 9,139,874 B2 * | 9/2015 | Myers | .......... C12Q 1/6869 |
| 2009/0026082 A1 | 1/2009 | Rothberg et al. | |
| 2009/0127589 A1 | 5/2009 | Rothberg et al. | |
| 2009/0325145 A1 | 12/2009 | Sablon et al. | |
| 2012/0109598 A1 | 5/2012 | Davey et al. | |
| 2012/0172241 A1 | 7/2012 | Rearick et al. | |
| 2012/0173158 A1 | 7/2012 | Hubbell | |
| 2012/0173159 A1 | 7/2012 | Davey et al. | |
| 2012/0264621 A1 | 10/2012 | Hubbell et al. | |
| 2013/0012399 A1 | 1/2013 | Myers et al. | |
| 2013/0060482 A1 | 3/2013 | Sikora et al. | |

OTHER PUBLICATIONS

Holt et al. The new paradigm of flow cell sequencing Genome Research vol. 18, pp. 839-846 (Year: 2008).*
Medvedev et al. Computational methods for discovering structural variation with next-generation sequencing Nature Methods Supplement vol. 6, pp. S13-S20 (Year: 2009).*
Sambrook et al., "Molecular Cloning: A Laboratory Manual", Third ed., Cold Spring Harbor Laboratory Press, Cold Spring Harbor, N.Y., 2000, cover pages and table of contents, 25 pages.
U.S. Appl. No. 61/584,391, specification, appendix, and drawings filed Jan. 9, 2012, 91 pages.

\* cited by examiner

*Primary Examiner* — John S Brusca

(57) ABSTRACT

Systems and methods for analyzing overlapping sequence information can obtain first and second overlapping sequence information for a polynucleotide, align the first and second sequence information, determine a degree of agreement between the first and second sequence information for a location along the polynucleotide, and determine a base call and a quality value for the location.

3 Claims, 10 Drawing Sheets

Specification includes a Sequence Listing.

SEQUENCE LISTING

```
<160> NUMBER OF SEQ ID NOS: 7

<210> SEQ ID NO 1
<211> LENGTH: 100
<212> TYPE: DNA
<213> ORGANISM: Artificial Sequence
<220> FEATURE:
<223> OTHER INFORMATION: Description of Artificial Sequence: Synthetic
      Ordering of Nucleotide Species Flows

<400> SEQUENCE: 1
tacgtacgtc tgagcatcga tcgatgtaca gctacgtacg tctgagcatc gatcgatgta    60
cagctacgta cgtctgagca tcgatcgatg tacagctacg                         100

<210> SEQ ID NO 2
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      Ordering of Nucleotide Species Flows

<400> SEQUENCE: 2
gatgtacagc tacgtacgtc tgagcatc                                            28

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      called bases of artificial sequence

<400> SEQUENCE: 3
gcacactttt tcaacatc                                                       18

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      called bases of artificial sequence

<400> SEQUENCE: 4
cgtgtgaaaa gttgtag                                                        17

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic
      Ordering of Nucleotide Species Flows

<400> SEQUENCE: 5
catgcatcga catgtagcta gctacgagtc tg                                       32

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      Ordering of Nucleotide Species Flows

<400> SEQUENCE: 6
gtctgagcat cgatcgatgt acagctacgt ac                                       32

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      called bases of artificial sequence

<400> SEQUENCE: 7
gatgttgaaa agtgtgc                                                        17
```

SYSTEMS AND METHODS FOR PAIRED END SEQUENCING

RELATED APPLICATIONS

This application is a Division of U.S. application Ser. No. 13/787,221 filed Mar. 6, 2013, which claims priority to U.S. application No. 61/640,288 filed Apr. 30, 2012, which disclosures are herein incorporated by reference in their entirety.

SEQUENCE LISTING

The instant application contains a Sequence Listing which has been submitted electronically in ASCII format and is hereby incorporated by reference in its entirety. Said ASCII copy, created on Mar. 17, 2022, is named LT00672DIV_SL.txt and is 2,180 bytes in size.

FIELD

The present disclosure generally relates to the field of nucleic acid sequencing including systems and methods for paired end sequencing.

INTRODUCTION

Upon completion of the Human Genome Project, one focus of the sequencing industry has shifted to finding higher throughput and/or lower cost nucleic acid sequencing technologies, sometimes referred to as "next generation" sequencing (NGS) technologies. In making sequencing higher throughput and/or less expensive, the goal is to make the technology more accessible. These goals can be reached through the use of sequencing platforms and methods that provide sample preparation for samples of significant complexity, sequencing larger numbers of samples in parallel (for example through use of barcodes and multiplex analysis), and/or processing high volumes of information efficiently and completing the analysis in a timely manner. Various methods, such as, for example, sequencing by synthesis, sequencing by hybridization, and sequencing by ligation are evolving to meet these challenges.

Ultra-high throughput nucleic acid sequencing systems incorporating NGS technologies typically produce a large number of short sequence reads. Sequence processing methods should desirably assemble and/or map a large number of reads quickly and efficiently, such as to minimize use of computational resources. For example, data arising from sequencing of a mammalian genome can result in tens or hundreds of millions of reads that typically need to be assembled before they can be further analyzed to determine their biological, diagnostic and/or therapeutic relevance.

Exemplary applications of NGS technologies include, but are not limited to: genomic resequencing including genomic variant detection, such as insertions/deletions, copy number variations, single nucleotide polymorphisms, etc., gene expression analysis and genomic profiling.

Of particular interest are improved systems and methods for detecting somatic mutations, such as those found in cancerous tumors. For example, identification of a somatic mutation specific to a cancerous tumor and not found in normal tissue can lead to insights into the development of cancer, aid in the discovery of new cancer treatments, or guide the selection of appropriate treatments for a cancer patient.

From the foregoing it will be appreciated that a need exists for systems and methods that can identify somatic mutations using nucleic acid sequencing data.

DRAWINGS

For a more complete understanding of the principles disclosed herein, and the advantages thereof, reference is now made to the following descriptions taken in conjunction with the accompanying drawings, in which:

FIG. 3 discloses SEQ ID NO: 1.

FIG. 8 discloses SEQ ID NOS 2-5, 4, and 6-7, respectively, in order of appearance.

Figure 1:
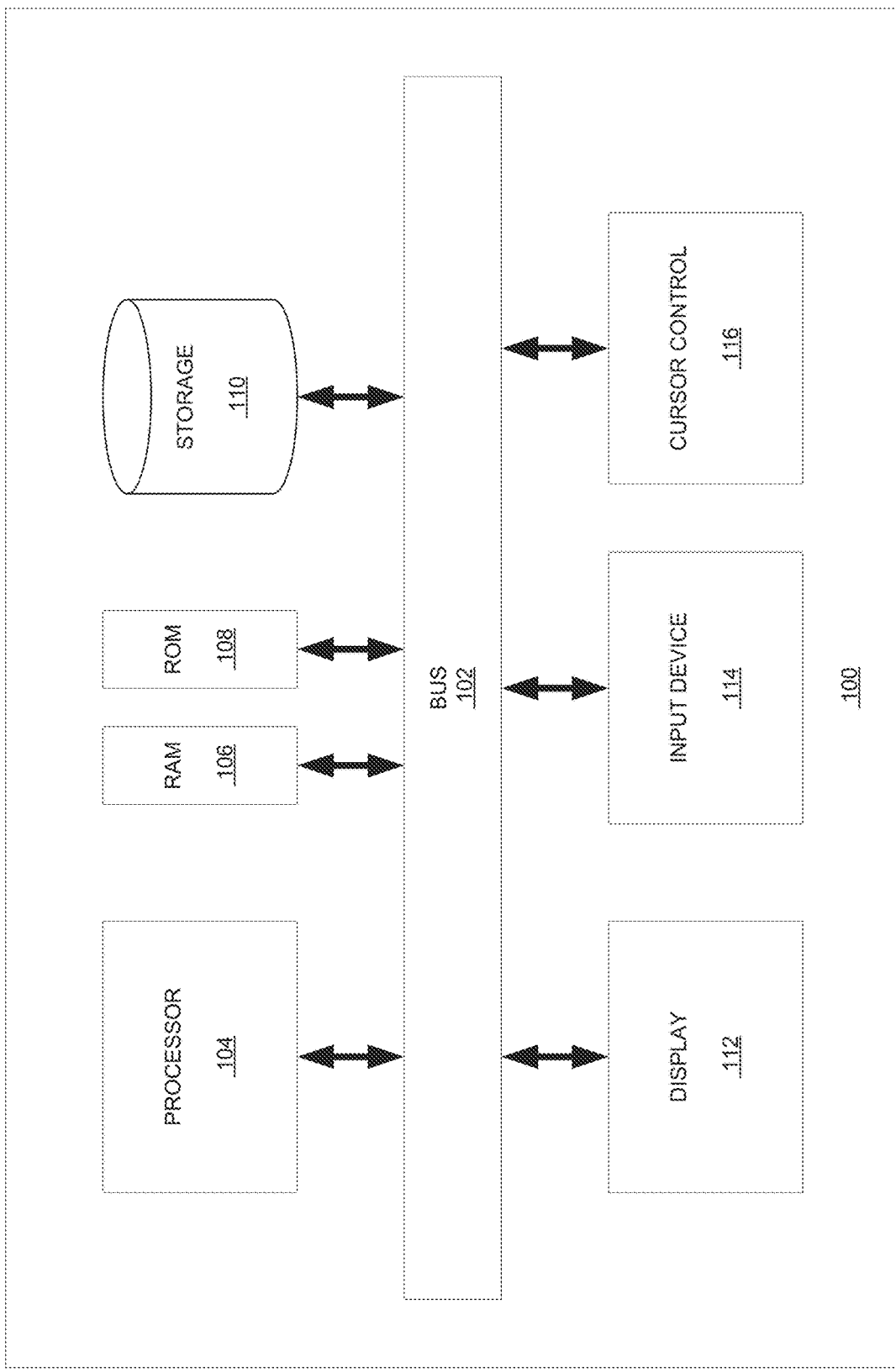
FIG. 1 is a block diagram that illustrates an exemplary computer system, in accordance with various embodiments.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DESCRIPTION OF VARIOUS EMBODIMENTS

Embodiments of systems and methods for detecting low frequency variants are described herein.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless described otherwise, all technical and scientific terms used herein have a meaning as is commonly understood by one of ordinary skill in the art to which the various embodiments described herein belongs.

It will be appreciated that there is an implied "about" prior to the temperatures, concentrations, times, number of bases, coverage, etc. discussed in the present teachings, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

As used herein, "a" or "an" also may refer to "at least one" or "one or more." Also, the use of "or" is inclusive, such that the phrase "A or B" is true when "A" is true, "B" is true, or both "A" and "B" are true.

Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. 2000). The nomenclatures utilized in connection with, and the laboratory procedures and techniques described herein are those well known and commonly used in the art.

A "system" sets forth a set of components, real or abstract, comprising a whole where each component interacts with or is related to at least one other component within the whole.

A "biomolecule" may refer to any molecule that is produced by a biological organism, including large polymeric molecules such as proteins, polysaccharides, lipids, and nucleic acids (DNA and RNA) as well as small molecules such as primary metabolites, secondary metabolites, and other natural products.

The phrase "next generation sequencing" or NGS refers to sequencing technologies having increased throughput as compared to traditional Sanger- and capillary electrophoresis-based approaches, for example with the ability to generate hundreds of thousands of relatively small sequence reads at a time. Some examples of next generation sequencing techniques include, but are not limited to, sequencing by synthesis, sequencing by ligation, and sequencing by hybridization. More specifically, the Personal Genome Machine (PGM) of Life Technologies Corp. provides massively parallel sequencing with enhanced accuracy. The PGM System and associated workflows, protocols, chemistries, etc. are described in more detail in U.S. Patent Application Publication No. 2009/0127589 and No. 2009/0026082, the entirety of each of these applications being incorporated herein by reference.

The phrase "sequencing run" refers to any step or portion of a sequencing experiment performed to determine some information relating to at least one biomolecule (e.g., nucleic acid molecule).

The phase "base space" refers to a representation of the sequence of nucleotides. The phase "flow space" refers to a representation of the incorporation event or non-incorporation event for a particular nucleotide flow. For example, flow space can be a series of zeros and ones representing a nucleotide incorporation event (a one, "1") or a non-incorporation event (a zero, "0") for that particular nucleotide flow. It should be understood that zeros and ones are convenient representations of a non-incorporation event and a nucleotide incorporation event; however, any other symbol or designation could be used alternatively to represent and/or identify these events and non-events.

To illustrate the interplay between base-space vectors, flow-space vectors, and nucleotide flow orders, one may consider, for example, an underlying template sequence beginning with "TA" subjected to multiple cycles of a nucleotide flow order of "TACG." The first flow, "T," would result in a non-incorporation because it is not complementary to the template's first base, "T." In the base-space vector, no nucleotide designation would be inserted; in the flow-space vector, a "0" would be inserted, leading to "0." The second flow, "A," would result in an incorporation because it is complementary to the template's first base, "T." In the base-space vector, an "A" would be inserted, leading to "A"; in the flow-space vector, a "1" would be inserted, leading to "01." The third flow "C" would result in a non-incorporation because it is not complementary to the template's second base, "A." In the base-space vector, no nucleotide designation would be inserted; in the flow-space vector, a "0" would be inserted, leading to "010." The fourth flow, "G," would result in a non-incorporation because it is not complementary to the template's second base, "A." In the base-space vector, no nucleotide designation would be inserted; in the flow-space vector, a "0" would be inserted, leading to "0100." The fifth flow "T" would result in an incorporation because it is complementary to the template's second base, "A." In the base-space vector, a "T" would be inserted, leading to "AT"; in the flow-space vector, a "1" would be inserted, leading to "01 001." (Note: if the analysis were to contemplate a potentially longer template, an "X" could be inserted here instead because additional "A's" could potentially be present in the template in the case of a longer homopolymer, which would allow for more than one incorporations during the fifth flow, leading to "01 OOX.") The base-space vector thus shows only the sequence of incorporated nucleotides, whereas the flowspace vector shows more expressly the incorporation status corresponding to each flow. Whereas a base-space representation may be fixed and remain common for various flow orders, the flow-based representation depends on the particular flow order. Knowing the nucleotide flow order, one can infer either vector from the other. Of course, the base-space vector could be represented using complementary bases rather than the incorporated bases (thus, one could just as well define the base-space representation of a sequencing key as being the incorporated nucleotides or as being the complementary nucleotides of the template against which the flowed nucleotides would be incorporated).

DNA (deoxyribonucleic acid) is a chain of nucleotides consisting of 4 types of nucleotides; A (adenine), T (thymine), C (cytosine), and G (guanine), and that RNA (ribonucleic acid) is comprised of 4 types of nucleotides; A, U (uracil), G, and C. Certain pairs of nucleotides specifically bind to one another in a complementary fashion (called complementary base pairing). That is, adenine (A) pairs with thymine (T) (in the case of RNA, however, adenine (A) pairs with uracil (U)), and cytosine (C) pairs with guanine (G). When a first nucleic acid strand binds to a second nucleic acid strand made up of nucleotides that are complementary to those in the first strand, the two strands bind to form a double strand. As used herein, "nucleic acid sequencing data," "nucleic acid sequencing information," "nucleic acid sequence," "genomic sequence," "genetic sequence," or "fragment sequence," or "nucleic acid sequencing read" denotes any information or data that is indicative of the order of the nucleotide bases (e.g., adenine, guanine, cytosine, and thymine/uracil) in a molecule (e.g., whole genome, whole transcriptome, exome, oligonucleotide, polynucleotide, fragment, etc.) of DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

A "polynucleotide", "nucleic acid", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Usually oligonucleotides range in size from a few monomeric units, e.g. 3-4, to several hundreds of monomeric units. Whenever a polynucleotide such as an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

As used herein, the phrase "paired end sequencing" or "paired end reads" can refer to sequencing techniques generally known in the art of molecular biology that can allow the determination of multiple "reads" of sequence, each from a different place on a single polynucleotide. In various embodiments, two reads can be in opposite directions along the polynucleotide and can have regions of overlap. Because the overlapping portions provide redundant information for a region of the polynucleotide, the use of the information from paired end reads can be used to correct errors during sequencing of a read, thereby improving the accuracy of the determined sequence.

Computer-implemented System

FIG. 1 is a block diagram that illustrates a computer system 100, upon which embodiments of the present teachings may be implemented. In various embodiments, computer system 100 can include a bus 102 or other communication mechanism for communicating information, and a processor 104 coupled with bus 102 for processing information. In various embodiments, computer system 100 can also include a memory 106, which can be a random access memory (RAM) or other dynamic storage device, coupled to bus 102 for determining base calls, and instructions to be executed by processor 104. Memory 106 also can be used for storing temporary variables or other intermediate information during execution of instructions to be executed by processor 104. In various embodiments, computer system 100 can further include a read only memory (ROM) 108 or other static storage device coupled to bus 102 for storing static information and instructions for processor 104. A storage device 110, such as a magnetic disk or optical disk, can be provided and coupled to bus 102 for storing information and instructions.

In various embodiments, computer system 100 can be coupled via bus 102 to a display 112, such as a cathode ray tube (CRT) or liquid crystal display (LCD), for displaying information to a computer user. An input device 114, including alphanumeric and other keys, can be coupled to bus 102 for communicating information and command selections to processor 104. Another type of user input device is a cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results can be provided by computer system 100 in response to processor 104 executing one or more sequences of one or more instructions contained in memory 106. Such instructions can be read into memory 106 from another computer-readable medium, such as storage device 110. Execution of the sequences of instructions contained in memory 106 can cause processor 104 to perform the processes described herein. Alternatively hard-wired circuitry can be used in place of or in combination with software instructions to implement the present teachings. Thus implementations of the present teachings are not limited to any specific combination of hardware circuitry and software.

The term "computer-readable medium" as used herein refers to any media that participates in providing instructions to processor 104 for execution. Such a medium can take many forms, including but not limited to, non-volatile media, volatile media, and transmission media. Examples of non-volatile media can include, but are not limited to, optical or magnetic disks, such as storage device 110. Examples of volatile media can include, but are not limited to, dynamic memory, such as memory 106. Examples of transmission media can include, but are not limited to, coaxial cables, copper wire, and fiber optics, including the wires that comprise bus 102.

Common forms of non-transitory computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

Nucleic Acid Sequencing Platforms

Nucleic acid sequence data can be generated using various techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, nanopore based systems, etc.

Figure 2:
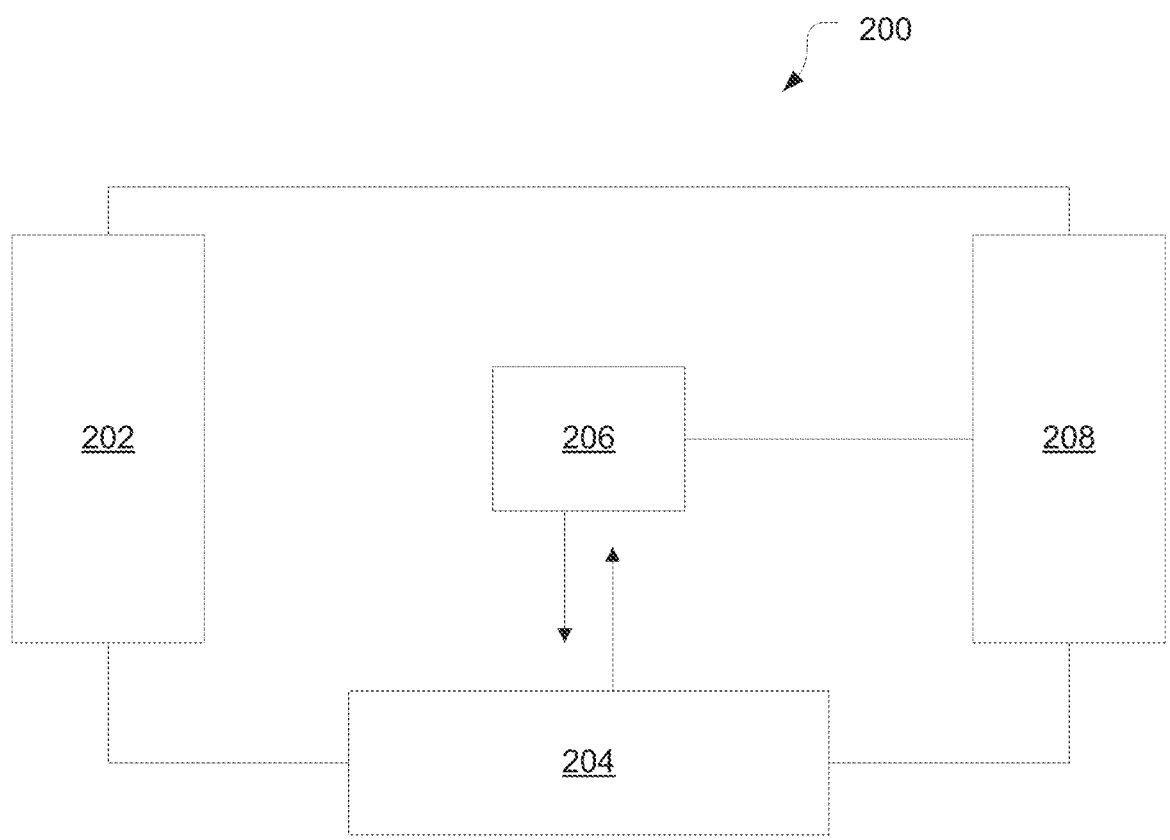
FIG. 2 is a schematic diagram of an exemplary system for determining a nucleic acid sequence, in accordance with various embodiments.

Various embodiments of nucleic acid sequencing platforms, such as a nucleic acid sequencer, can include components as displayed in the block diagram of FIG. 2. According to various embodiments, sequencing instrument 200 can include a fluidic delivery and control unit 202, a sample processing unit 204, a signal detection unit 206, and a data acquisition, analysis and control unit 208. Various embodiments of instrumentation, reagents, libraries and methods used for next generation sequencing are described in U.S. Patent Application Publication No. 2009/0127589 and No. 2009/0026082 are incorporated herein by reference. Various embodiments of instrument 200 can provide for automated sequencing that can be used to gather sequence information from a plurality of sequences in parallel, such as substantially simultaneously.

In various embodiments, the fluidics delivery and control unit 202 can include reagent delivery system. The reagent delivery system can include a reagent reservoir for the storage of various reagents. The reagents can include nucleotide tri-phosphates (such as ATP, CTP, GTP, TTP), RNA-based primers, forward/reverse DNA primers, oligonucleotide mixtures for ligation sequencing, nucleotide mixtures for sequencing-by-synthesis, buffers, wash reagents, blocking reagent, stripping reagents, and the like. Additionally, the reagent delivery system can include a pipetting system or a continuous flow system which connects the sample processing unit with the reagent reservoir.

In various embodiments, the sample processing unit 204 can include a sample chamber, such as flow cell, a substrate, a micro-array, a multi-well tray, or the like. The sample processing unit 204 can include multiple lanes, multiple channels, multiple wells, or other means of processing multiple sample sets substantially simultaneously. Additionally, the sample processing unit can include multiple sample chambers to enable processing of multiple runs simultaneously. In particular embodiments, the system can perform signal detection on one sample chamber while substantially simultaneously processing another sample chamber. Additionally, the sample processing unit can include an automation system for moving or manipulating the sample chamber.

In various embodiments, the signal detection unit 206 can include an imaging or detection sensor. For example, the imaging or detection sensor can include a CCD, a CMOS, an ion or chemical sensor, such as an ion sensitive layer overlying a CMOS or FET, a current or voltage detector, or the like. The signal detection unit 206 can include an excitation system to cause a probe, such as a fluorescent dye, to emit a signal. The excitation system can include an illumination source, such as arc lamp, a laser, a light emitting diode (LED), or the like. In particular embodiments, the signal detection unit 206 can include optics for the transmission of light from an illumination source to the sample or from the sample to the imaging or detection sensor. Alternatively, the signal detection unit 206 may provide for electronic or non-photon based methods for detection and consequently not include an illumination source. In various embodiments, electronic-based signal detection may occur when a detectable signal or species is produced during a sequencing reaction. For example, a signal can be produced by the interaction of a released byproduct or moiety, such as a released ion, such as a hydrogen ion, interacting with an ion or chemical sensitive layer. In other embodiments a detectable signal may arise as a result of an enzymatic cascade such as used in pyrosequencing (see, for example, U.S. Patent Application Publication No. 2009/0325145, the entirety of which being incorporated herein by reference) where pyrophosphate is generated through base incorporation by a polymerase which further reacts with ATP sulfurylase to generate ATP in the presence of adenosine 5' phosphosulfate wherein the ATP generated may be consumed in a luciferase mediated reaction to generate a chemiluminescent signal. In another example, changes in an electrical current can be detected as a nucleic acid passes through a nanopore without the need for an illumination source.

In various embodiments, a data acquisition analysis and control unit 208 can monitor various system parameters. The system parameters can include temperature of various portions of instrument 200, such as sample processing unit or reagent reservoirs, volumes of various reagents, the status of various system subcomponents, such as a manipulator, a stepper motor, a pump, or the like, or any combination thereof.

It will be appreciated by one skilled in the art that various embodiments of instrument 200 can be used to practice variety of sequencing methods including ligation-based methods, sequencing by synthesis, single molecule methods, nanopore sequencing, and other sequencing techniques.

In various embodiments, the sequencing instrument 200 can determine the sequence of a nucleic acid, such as a polynucleotide or an oligonucleotide. The nucleic acid can include DNA or RNA, and can be single stranded, such as ssDNA and RNA, or double stranded, such as dsDNA or a RNA/cDNA pair. In various embodiments, the nucleic acid can include or be derived from a fragment library, a mate pair library, a ChIP fragment, or the like. In particular embodiments, the sequencing instrument 200 can obtain the sequence information from a single nucleic acid molecule or from a group of substantially identical nucleic acid molecules.

In various embodiments, sequencing instrument 200 can output nucleic acid sequencing read data in a variety of different output data file types/formats, including, but not limited to: *.fasta, *.csfasta, *seq.txt, *qseq.txt, *.fastq, *.sff, *prb.txt, *.sms, *srs and/or *.qv.

In various embodiments, sequencing can be performed in bi-directional sequencing of a fragment by sequencing the fragment in both directions. For example, the sequencing instrument 200 can determine a first (forward) read of a nucleic acid while a forward primer can be extended in a forward direction along a single stranded template. The template can be prepared for a second (reverse) read. For example, the forward primer can be extended the full length of the template, and the template can be nicked and degraded to leave a portion that can act as a primer for the reverse read. The sequencing instrument 200 can determine the second (reverse) read while the reverse primer can be extended in the opposite direction along the extended forward primer. For example, bidirectional sequencing is described in more detail in co-pending U.S. application Ser. No. 13,543,521, filed Jul. 6, 2012 and titled "Sequencing Methods and Compositions", which is incorporated by reference in entirety.

Flow Space

Figure 3:
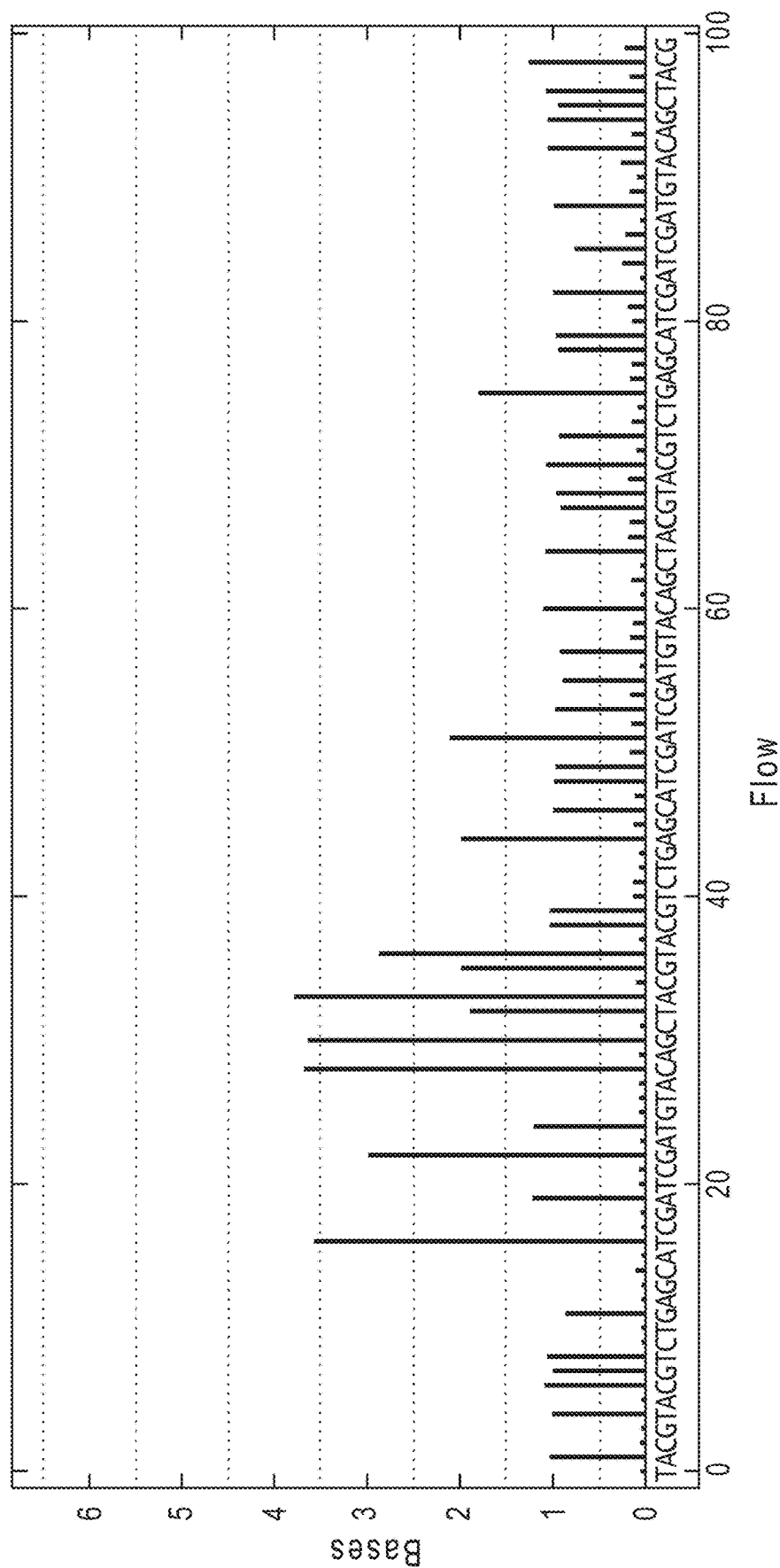
FIG. 3 is an exemplary ionogram in accordance with various embodiments.

FIG. 3 shows an exemplary ionogram representation of signals from which base calls may be made. In this example, the x-axis shows the nucleotide that is flowed and the corresponding number of nucleotide incorporations may be estimated by rounding to the nearest integer shown in the y-axis, for example. Signals used to make base calls and determine a flowspace vector may be from any suitable point in the acquisition or processing of the data signals received from sequencing operations. For example, the signals may be raw acquisition data or data having been processed, such as, e.g., by background filtering, normalization, correction for signal decay, and/or correction for phase errors or effects, etc. The base calls may be made by analyzing any suitable signal characteristics (e.g., signal amplitude or intensity).

In various embodiments, output signals due to nucleotide incorporation may be processed in various way to improve their quality and/or signal-to-noise ratio, which may include performing or implementing one or more of the teachings disclosed in Rearick et al., U.S. patent application Ser. No. 13/339,846, filed Dec. 29, 2011, and in Hubbell, U.S. patent application Ser. No. 13/339,753, filed Dec. 29, 2011, which are all incorporated by reference herein in their entirety.

In various embodiments, output signals due to nucleotide incorporation may be further processed, given knowledge of what nucleotide species were flowed and in what order to obtain such signals, to make base calls for the flows and compile consecutive base calls associated with a sample nucleic acid template into a read. A base call refers to a particular nucleotide identification (e.g., dATP ("A"), dCTP ("C"), dGTP ("G"), or dTTP ("T")). Base calling may include performing one or more signal normalizations, signal phase and signal droop (e.g, enzyme efficiency loss) estimations, and signal corrections, and may identify or estimate base calls for each flow for each defined space. Base calling may include performing or implementing one or more of the teachings disclosed in Davey et al., U.S. patent application Ser. No. 13/283,320, filed Oct. 27, 2011, which is incorporated by reference herein in its entirety. Other aspects of signal processing and base calling may include performing or implementing one or more of the teachings disclosed in Davey et al., U.S. patent application Ser. No. 13/340,490, filed on Dec. 29, 2011, and Sikora et al., U.S. patent application Ser. No. 13/588,408, filed on Aug. 17, 2012, which are all incorporated by reference herein in their entirety.

Figure 4:
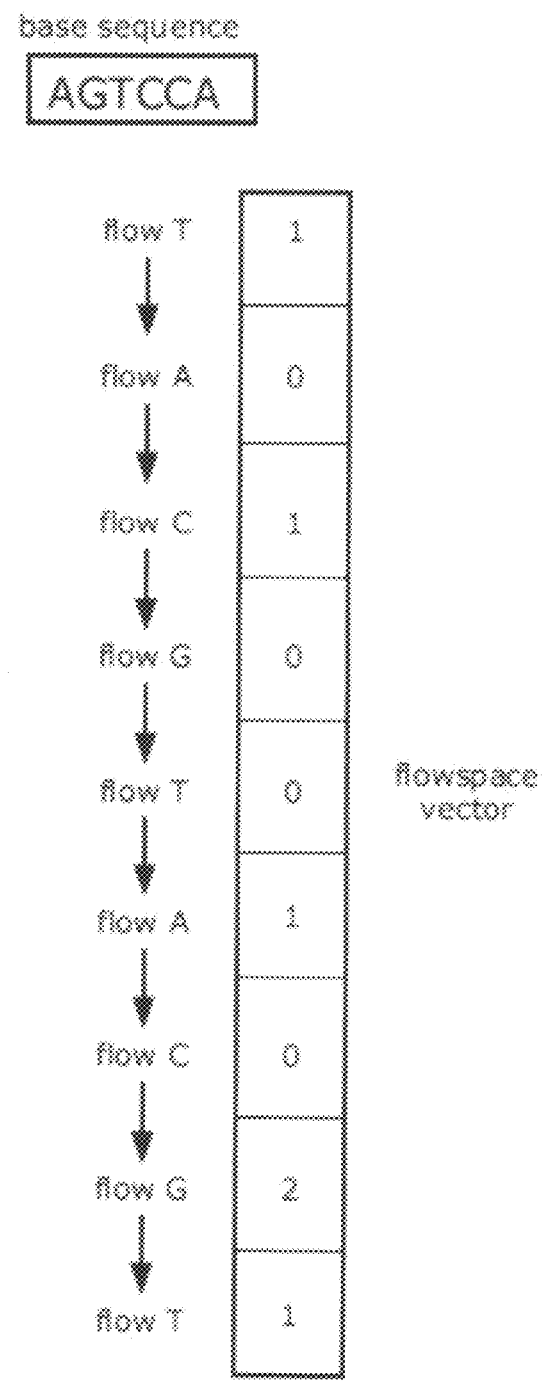
FIGS. 4 and 5 are illustrations of the relationship between flow space and base space, in accordance with various embodiments.
Figure 5:
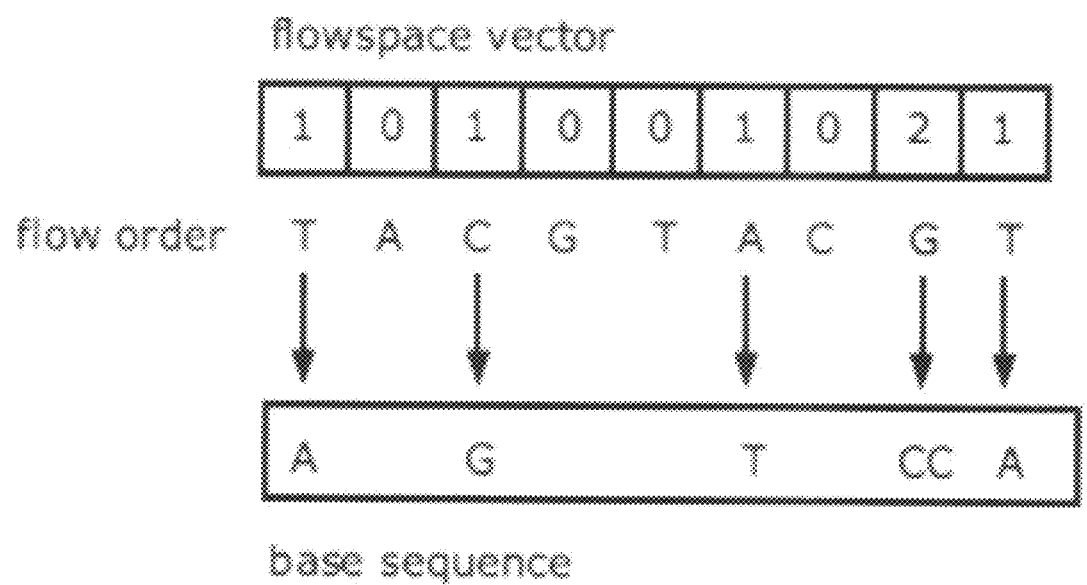

FIGS. 4 and 5 demonstrate a relationship between a base space sequence and a flowspace vector. A series of signals representative of a number of incorporations or lack thereof (e.g., 0-mer, 1-mer, 2-mer, etc.) produced by a series of nucleotide flows may be referred to as a flowspace vector or sequence, as opposed to a base space sequence, which is simply the order of identified nucleotide bases in a nucleic acid of interest. The flowspace vector may be produced using any suitable nucleotide flow ordering, including a predetermined ordering based on a cyclical, repeating pattern of consecutive repeats of a predetermined reagent flow ordering, based on a random reagent flow ordering, or based on an ordering comprising in whole or in part a phase-protecting reagent flow ordering as described in Hubbell et al., U.S. patent application Ser. No. 13/440,849, filed Apr. 5, 2012, or some combination thereof. In FIGS. 4 and 5, an exemplary base space sequence AGTCCA is subjected to sequencing operations using a cyclical flow ordering of TACG (that is, a T nucleotide flow, followed by an A nucleotide flow, followed by a C nucleotide flow, followed by a G nucleotide flow, and this 4-flow ordering is then repeated cyclically). The flows result in a series of signals, each signal having an amplitude (e.g., signal intensity) related to the number of nucleotide incorporations (e.g., 0-mer, 1-mer, 2-mer, etc.). This series of signals generates the flowspace vector 101001021. As shown in FIG. 4, the base space sequence AGTCCA may be translated to a flowspace vector 101001021 under a cyclical flow ordering of TACG. The flowspace vector may change if the flow ordering is changed. As shown in FIG. 5, the flowspace vector may be mapped back to the base space sequence associated with the sample.

System and Methods for Analyzing Paired End Read Information

Figure 6:
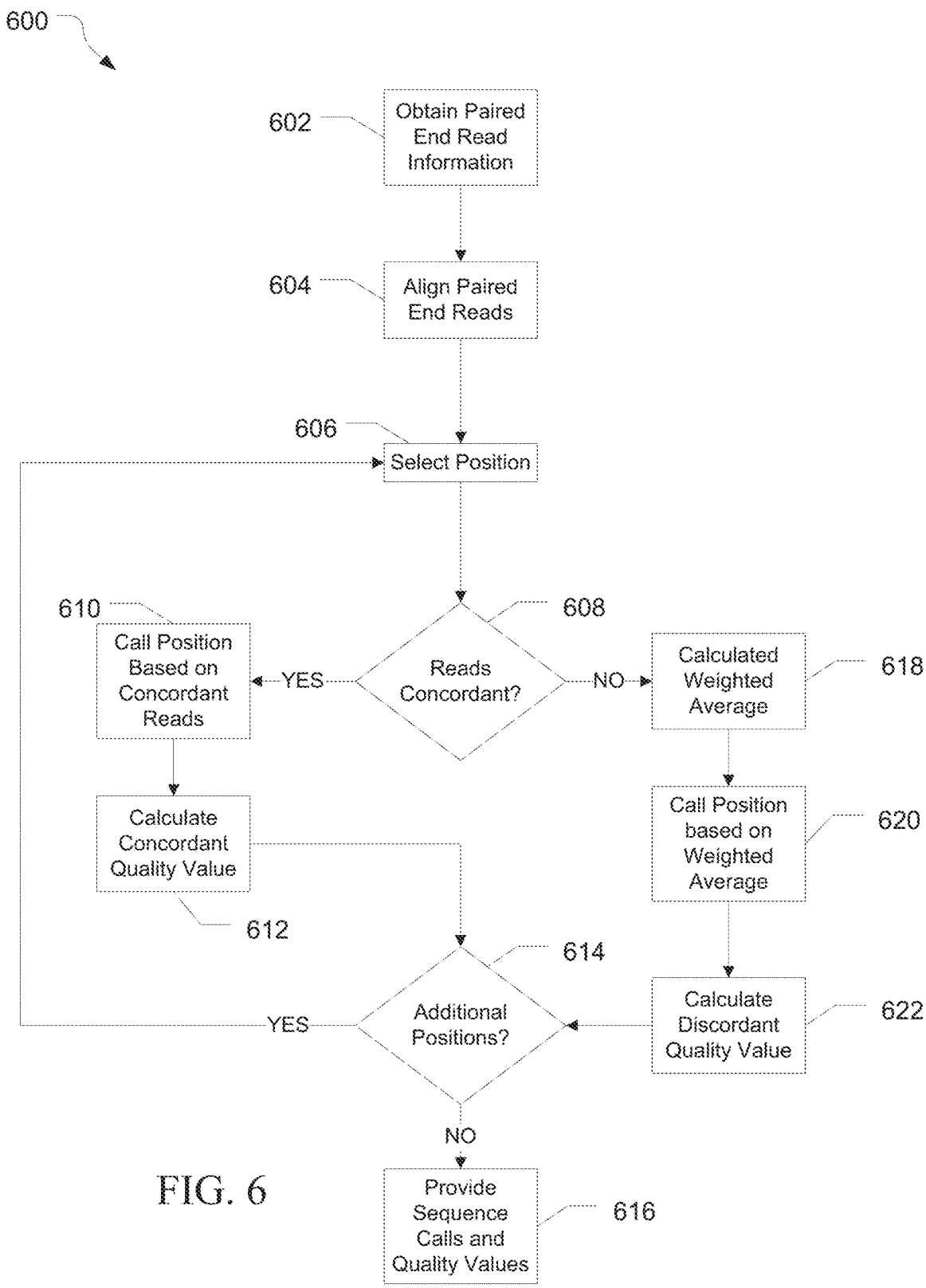
FIG. 6 is a flow diagram illustrating an exemplary method of analyzing paired end read information, in accordance with various embodiments.

FIG. 6 is an exemplary flow diagram showing a method 600 for analyzing paired end read information, in accordance with various embodiments. In various exemplary embodiment, multiple overlapping reads of the same polynucleotide can be used to correct sequencing errors in one of the reads, thereby improving the accuracy and confidence in the resulting sequence.

At 602, paired end read information can be obtained. In various exemplary embodiments, the paired end read information can be obtained by sequencing a polynucleotide from opposite directions, such as from 5'→3' and 3'→5'.

At 604, the paired end reads can be aligned to identify the overlapping regions of the reads. In various embodiments, the alignment can be performed in base space, flow space, color space, or other representations of the information received from a sequencing system. In particular embodiments, aligning the paired end reads in a signal space (such as flow space or color space) can prove to be advantageous. Specifically, by utilizing the signal information, combining information from ambiguous signals can provide sufficient evidence to confidently call the base sequence. For example, for a homopolymer stretch, flow space information from a first read may ambiguously indicate the homopolymer length as 4 to 5 bases, whereas flow space information from the paired second read may ambiguously indicate the homopolymer length as 3 to 4 bases. Whereas use of only base space information could result in an indication of a homopolymer length of 3 to 5 bases, using the signal space information can provide sufficient evidence to identify the homopolymer length as 4 bases.

At 606, a position can be selected in the overlapping region of the paired end reads. At 608, the paired end reads can be compared at the selected position to determine if the paired end reads are concordant, such that the paired end reads indicate agreement at the position.

At 610, when the paired end reads are concordant at a position, such as for example both reads provide evidence for C at the selected position, a call can be made for a consensus read at the selected position. At 612, a concordant quality value can be calculated for the selected position. In various embodiments, the concordant quality value can be greater than a quality value determined for a base call based on either read individually.

At 614, a determination can be made as to if there are additional positions in the overlapping region of the paired end reads. When there are additional positions, another position can be selected at 606. Alternatively, when there are no additional positions, the sequence calls and quality values can be provided, as indicated at 616.

Returning to 608, when the paired reads are not concordant, a weighted average of the signal information can be calculated for the position, as indicated at 618. In various embodiments, the accuracy of the reads may be different at a particular position. For example, the accuracy of the reads may decrease along the length of the read such as due to carry forward and incomplete extensions errors. As such, a signal from a read at a position closer to the beginning can be weighted more than a signal from a read at a position closer to the end. Additionally, as the sequence context may be different for the paired end reads, modeling of context dependent errors can be used to influence the weighting of the signals of the paired end reads.

At 620, a call may be made for the position based on the weighted average signal, and at 622, a discordant quality value can be determined. Discordant reads provide evidence that a sequencing error occurred at the position for at least one of the reads. The call can be made based on assumptions as to which read is less likely to be in error, but it may not be possible to tell in which read the sequencing error occurred. Thus, in various embodiments, the discordant quality value may be lower than a quality value determined for an individual read.

Figure 7:
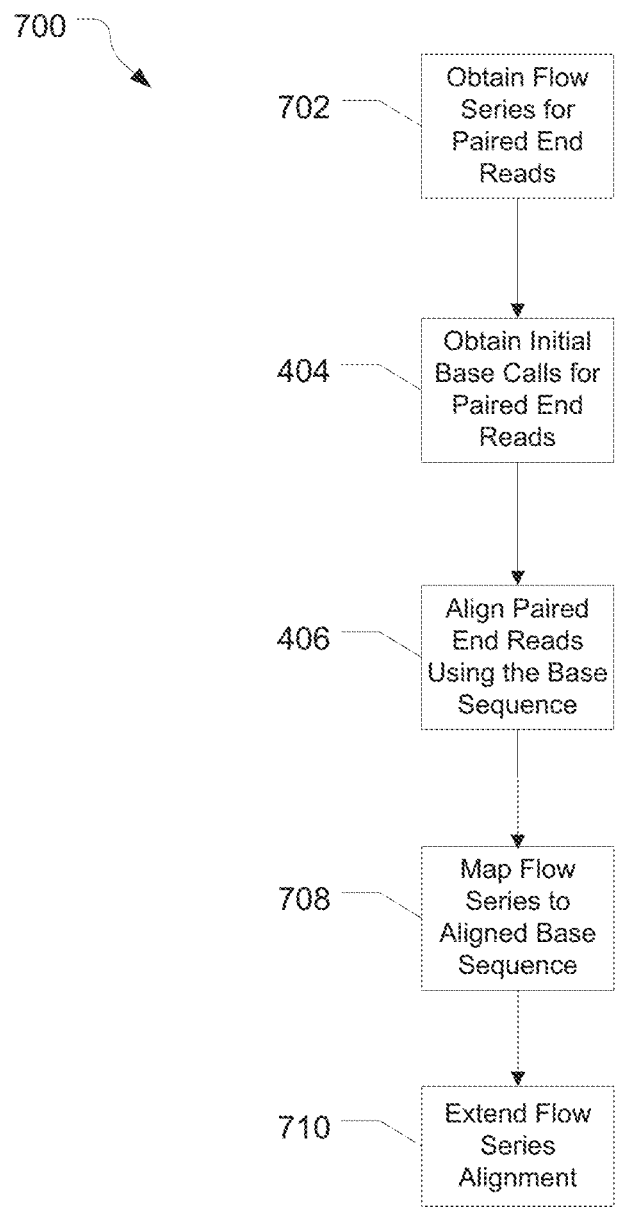
FIG. 7 is a flow diagram illustrating an exemplary method of aligning flow series information for paired end reads, in accordance with various embodiments.

FIG. 7 is an exemplary flow diagram illustrating a method of aligning flow series information for paired end reads, in accordance with various embodiments. A flow series includes information about the signals generated or observed by a sequencing instrument when a sample polynucleotide is exposed to a series of nucleotide flows, such as under conditions to allow synthesis of a complimentary polynucleotide. As the series of nucleotide flows may not precisely match the order of nucleotides incorporated into the complimentary polynucleotide, the flow series can contain "empty flows" indicative of a nucleotide flow that did not result in an incorporation of the nucleotide. Additionally, for a homopolymer stretch, a single nucleotide flow may result in multiple incorporations and result in a signal proportional to the number of incorporations. Further, the order of the nucleotide flows, "flow order", may vary, such that, for example, an 'A' is not always flowed after a 'C'. These factors can make the flow series information highly dependent on both the sequence context and the starting point for the read. Specifically, two reads of the same polynucleotide may have different numbers of empty flows between incorporation events depending on the starting point of the two reads. Thus, there may not be a 1:1 mapping of the flows for the two reads. Additionally, when the two reads are performed in opposite directions, such as 5'→3' and 3'→5', the sequence context for the two reads can be different.

At 702, flow series information can be obtained for paired end reads. In various exemplary embodiments, the flow series information can be obtained by sequencing a polynucleotide or the flow series information can be provided as a data file from a sequencing instrument.

At 404, initial base sequences for the paired end reads can be obtained. In various embodiments, the initial base sequences for the paired end reads can be provided as a file, such as along with the flow series information or in a separate file, or can be determined based on the flow series information. Various methods are known in the art for determining an initial base call, for example, a method of determining an initial base sequence is described in U.S. patent application Ser. No. 13/340,490, the entirety of which is incorporated herein by reference.

At 406, an initial alignment of the paired end reads can be determined using the base sequence for the reads. In various embodiments, the initial alignment can be limited to only a portion of the paired base sequence, such as not more than 100 bases, such as not more than 50 bases, even not more than 20 bases, or such as not more than one half of the base sequence length, such as not more than one fourth of the base sequence length, even not more than one tenth of the base sequence length. In various embodiments, as the paired end reads represent sequence data from the same polynucleotide, corresponding reads should be substantially concordant, only differing in positions where a sequencing error has occurred in at least one of the paired end reads. As such, the initial alignment may be a perfect match, such that over the length of the aligned portion no mismatches are present.

At 708, the flow series information for the reads can be mapped to the aligned base sequence. For example, the non-empty flows that correspond to the aligned base calls can be mapped to the aligned positions while empty flows in between the non-empty flows can be mapped between the positions. Where the empty flows of the flow series correspond, the empty flows can also be aligned.

By way of example, given an aligned sequence of CTG (corresponding to the complementary CAG in the reverse direction), a base space alignment can be defined as follows.

```
5' C T G 3'

3' G A C 5'
```

With corresponding flow orders of CAGTCAG and CTATG for the top and bottom reads respectively, the empty flows can be mapped as follows, with the lowercase letters representing the empty flows.

```
5' C a g T c a G 3'

3' G t    A    t C 5'
```

At 710, the flow series alignment can be extended in both directions by aligning non-empty flows with empty flows spaced between. Where there are corresponding empty flows, the empty flows can also be aligned.

Figure 8:
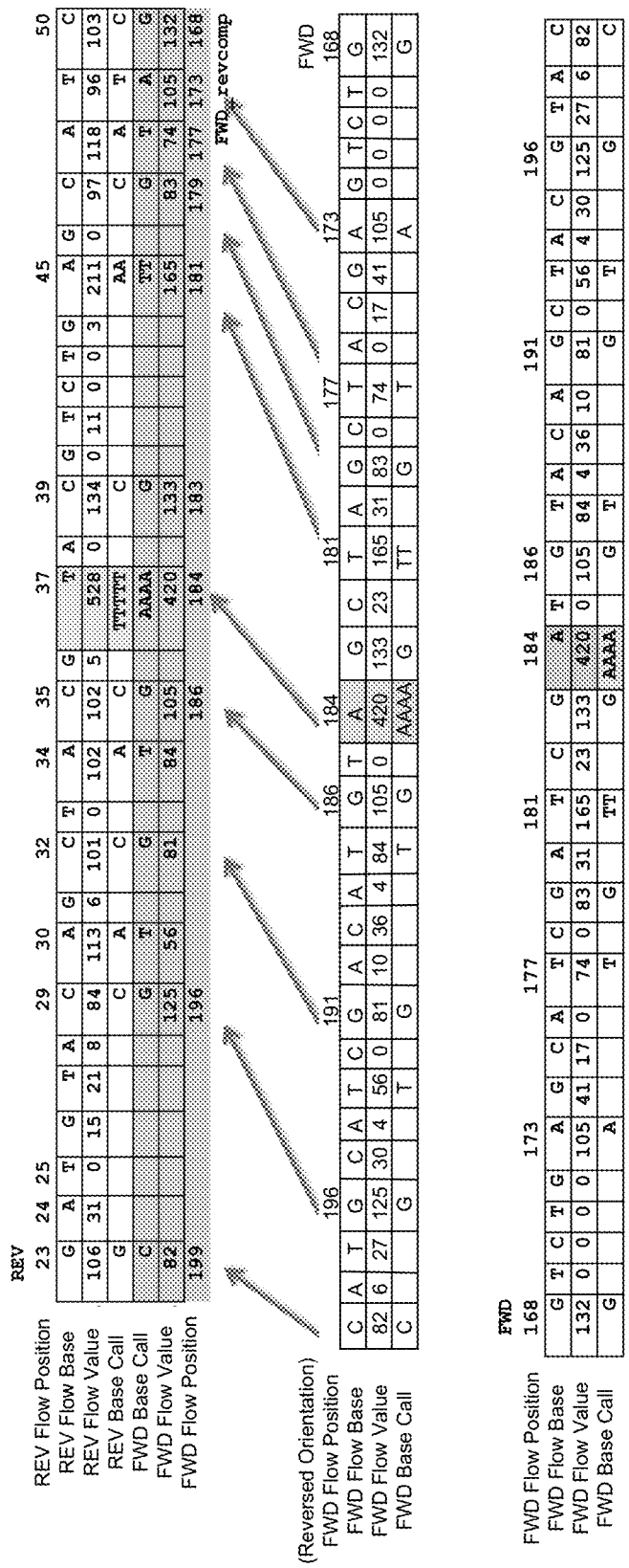
FIG. 8 is an illustration of a flow space alignment, in accordance with various embodiments.

FIG. 8 illustrates a flow space alignment for a forward (FWD) and reverse (REV) read of a fragment. For illustrative purposes, the orientation of the FWD flow vector is reversed to align orientations with the REV flow vector, and the positive flows of the FWD flow vector are mapped to the flow order of the REV flow vector. Alignment in flow space of the two reads allows a comparison of the flow values in addition to the base calls. In the example illustrated, flow position 37 of the REV read shows a homopolymer of 5 Ts with a flow value of 528. The corresponding position in the FWD read shows a homopolymer of 4 As with a flow value of 420. As a result, the confidence in the call at this position can be lower than the confidence in other calls where there is a consensus between the FWD and REV reads. Additionally, a consensus call can be made by taking a weighted average of the call. The value of the REV read may be have a higher weighting given it is earlier in the flow sequence (37 vs. 184).

Figure 9:
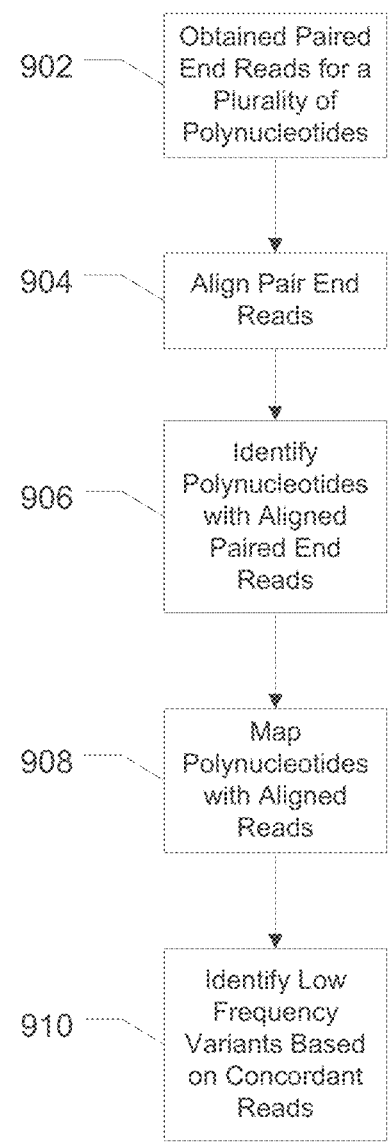
FIG. 9 is a flow diagram illustrating an exemplary method of analyzing paired end reads information to identify low frequency variants, in accordance with various embodiments.

FIG. 9 is a flow diagram illustrating an exemplary method of analyzing paired end read information to identify low frequency variants, in accordance with various embodiments.

At 902, paired end reads for a plurality of polynucleotides, such as from the same sample, can be obtained, and at 904, corresponding paired end reads can be aligned.

At 906, polynucleotides can be identified where the paired end reads are aligned. In various embodiments, paired end reads for a portion of the polynucleotides may not be able to be aligned. For example, when the length of the reads is relatively short compared to the length of the polynucleotide, there may be insufficient overlap of the reads. In another example, when there is a large number of sequencing errors for a read, it may not be possible to identify a sufficiently large region with an alignment having no mismatches. Regardless of the reason, polynucleotides where there is not an alignment of the paired end reads can be excluded from further analysis.

At 908, consensus sequences from polynucleotides with aligned reads can be mapped, such as to a reference sequence or to one another, and the sequences can be compared to identify variants, as indicated at 910. Various methods are known in the art for identifying variants, for example, a method of identifying variants is described in U.S. Provisional Patent Application No. 61/584,391, the entirety of which is incorporated herein by reference and included as Exhibit 1.

Generally, where the paired end reads are concordant, there is a high degree of confidence that there are not sequencing errors for the paired end reads at that position. For example, if there is an expected error rate of about 1% (0.01), the expected likelihood of an error occurring in two paired end reads at the same position would be about 0.01% (0.0001). Thus by analyzing only concordant reads at a position, the expected error rate can be significantly decreased and low frequency variants may be identified with confidence at lower frequencies than with data from the entire sample at a higher expected error rate.

Figure 10:
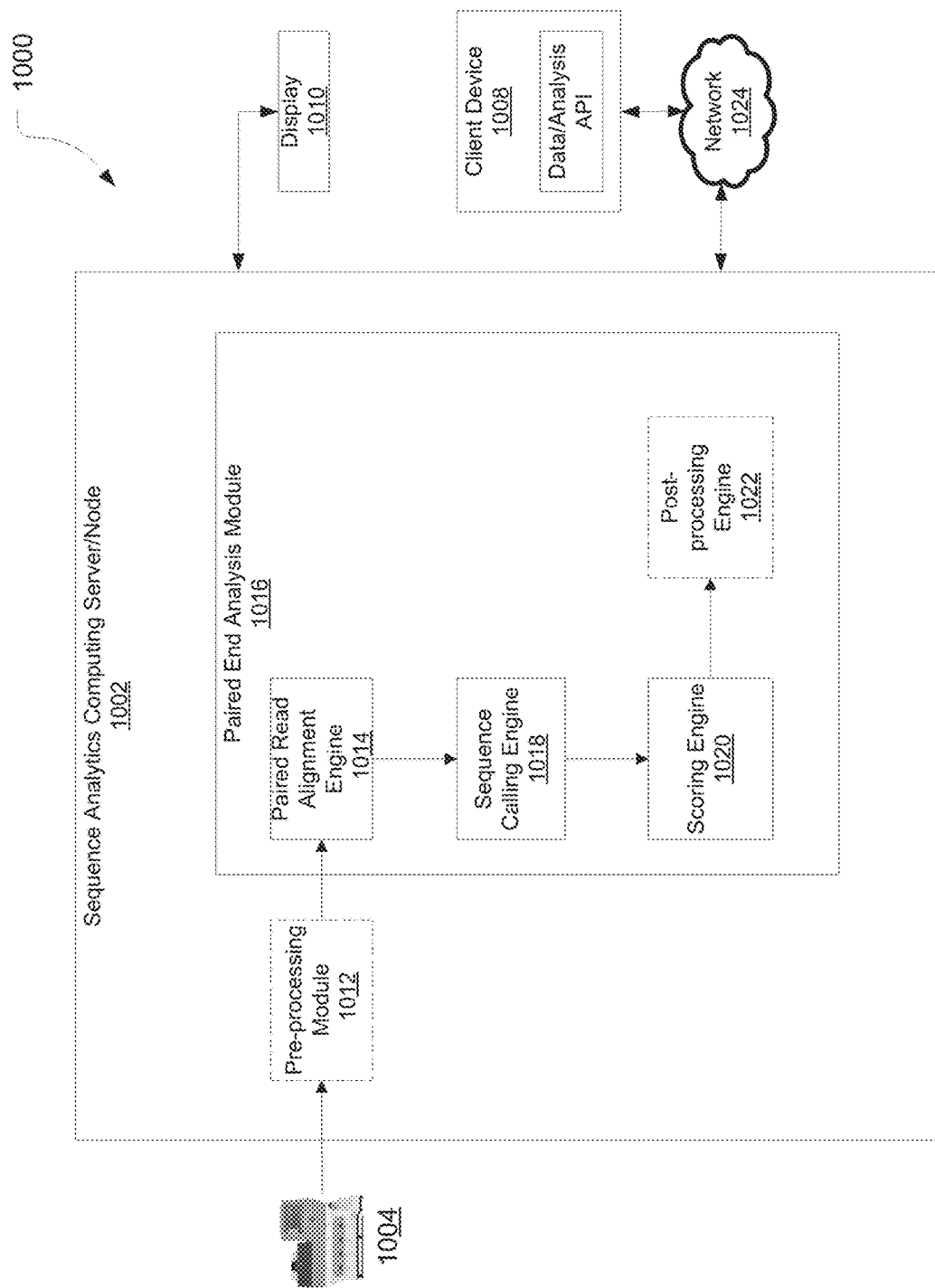
FIG. 10 is a schematic diagram of an exemplary genetic analysis system, in accordance with various embodiments.

FIG. 10 is a schematic diagram of a system for identifying variants, in accordance with various embodiments.

As depicted herein, sequence analysis system 1000 can include a nucleic acid sequence analysis device 1004 (e.g., nucleic acid sequencer, real-time/digital/quantitative PCR instrument, microarray scanner, etc.), a sequence analytics computing server/node/device 1002, and a display 1010 and/or a client device terminal 1008.

In various embodiments, the sequence analytics computing server/node/device 1002 can be communicatively connected to the nucleic acid sequence analysis device 1004, and client device terminal 1008 via a network connection 1024 that can be either a "hardwired" physical network connection (e.g., Internet, LAN, WAN, VPN, etc.) or a wireless network connection (e.g., Wi-Fi, WLAN, etc.).

In various embodiments, the sequence analytics computing device/server/node 1002 can be a workstation, mainframe computer, distributed computing node (such as, part of a "cloud computing" or distributed networking system), personal computer, mobile device, etc. In various embodiments, the nucleic acid sequence analysis device 1004 can be a nucleic acid sequencer, real-time/digital/quantitative PCR instrument, microarray scanner, etc. It should be understood, however, that the nucleic acid sequence analysis device 1004 can essentially be any type of instrument that can generate nucleic acid sequence data from samples obtained from an individual.

The sequence analytics computing server/node/device 1002 can be configured to host an optional pre-processing module 1012, and a paired end analysis module 1016.

Pre-processing module 1012 can be configured to receive information from the nucleic acid sequence analysis device 1004 and perform preprocessing steps, such as conversion from f space to base space, from color space to base space, or from flow space to base space, determining initial call quality values, preparing the read data for use by the paired end analysis module 1016, and the like.

The paired end analysis module 1016 can include a paired read alignment engine 1014, a sequence calling engine 1018, a scoring engine 1020, and an optional post processing engine 1022. In various embodiments, paired end analysis module 1016 can be in communications with the preprocessing module 1012. That is, the paired end analysis module 1016 can request and receive data and information (through, e.g., data streams, data files, text files, etc.) from preprocessing module 1012.

The paired reads alignment engine 1014 can be configured to receive paired end reads from the preprocessing module 1012, align the paired end reads, and provide the aligned paired end reads to the sequence calling engine 1018.

In various embodiments, the alignment of the sequence fragment and reference sequence can include a limited number of mismatches between a first paired end read and a second paired end read. Generally, a portion of the first paired end read sequence can be aligned to a portion of the second paired end read sequence in order to minimize the number of mismatches between the first and second paired end read sequences.

The sequence calling engine 1018 can be configured to receive aligned paired end reads from the paired end read alignment engine 1014, analyze the alignments to identify concordant and discordant positions, determine consensus base calls for the aligned portions, and provide the calls and signal information to the scoring engine 1020.

Scoring engine 1020 can be configured to receive the calls and signal information from the sequence calling engine 1018, and determine a quality value for the calls. The quality value can represent a likelihood that the call accurately represents the sequence of the polynucleotide at the position and can be based on the signal information for the paired end reads and the agreement between the paired end reads.

Post processing engine 1022 can be configured to receive the called sequence and quality values and perform additional processing steps. For example, the post processing engine 1022 may filter the reads, such as by selecting only aligned portions of the paired end reads and discarding unaligned portions or reads that were not found to align or overlap with a corresponding paired end read. Further, the post processing engine 1022 can format the sequence data for display on display 1010 or use by client device 1008.

Client device 1008 can be a thin client or thick client computing device. In various embodiments, client terminal 1008 can have a web browser (e.g., INTERNET EXPLORER™, FIREFOX™, SAFARI™, etc) that can be used to communicate information to and/or control the operation of the pre-processing module 1012, paired read alignment engine 1014, sequence calling engine 1018, scoring engine 1020, and post processing engine 1022 using a browser to control their function. For example, the client terminal 1008 can be used to configure the operating parameters (e.g., match scoring parameters, annotations parameters, filtering parameters, data security and retention parameters, etc.) of the various modules, depending on the requirements of the particular application. Similarly, client terminal 1008 can also be configure to display the results of the analysis performed by the variant calling module 1016 and the nucleic acid sequencer 1004.

It should be understood that the various data stores disclosed as part of system 1000 can represent hardware-based storage devices (e.g., hard drive, flash memory, RAM, ROM, network attached storage, etc.) or instantiations of a database stored on a standalone or networked computing device(s).

It should also be appreciated that the various data stores and modules/engines shown as being part of the system 1000 can be combined or collapsed into a single module/engine/data store, depending on the requirements of the particular application or system architecture. Moreover, in various embodiments, the system 1000 can comprise additional modules, engines, components or data stores as needed by the particular application or system architecture.

In various embodiments, the system 1000 can be configured to process the nucleic acid reads in color space. In various embodiments, system 1000 can be configured to process the nucleic acid reads in base space. In various embodiments, system 1000 can be configured to process the nucleic acid sequence reads in flow space. It should be understood, however, that the system 1000 disclosed herein can process or analyze nucleic acid sequence data in any schema or format as long as the schema or format can convey the base identity and position of the nucleic acid sequence.

In various embodiments, the methods of the present teachings may be implemented in a software program and applications written in conventional programming languages such as C, C++, etc.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The embodiments described herein, can be practiced with other computer system configurations including hand-held devices, microprocessor systems, microprocessor-based or programmable consumer electronics, minicomputers, mainframe computers and the like. The embodiments can also be practiced in distributing computing environments where tasks are performed by remote processing devices that are linked through a network.

It should also be understood that the embodiments described herein can employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations that form part of the embodiments described herein are useful machine operations. The embodiments, described herein, also relate to a device or an apparatus for performing these operations. The systems and methods described herein can be specially constructed for the required purposes or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

Certain embodiments can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CD-RWs, magnetic tapes, and other optical and non-optical data storage devices. The computer readable medium can also be distributed over a network coupled computer systems so that the computer readable code is stored and executed in a distributed fashion.

What is claimed is:

1. A method of analyzing overlapping sequence information, comprising:

sequencing a target nucleic acid in a first direction to obtain a first sequence signal information wherein sequencing in the first direction includes extending a first primer in the first direction;

removing a portion of the target nucleic acid after sequencing in the first direction, leaving the extended first primer and a portion of the target nucleic acid to act as a second primer;

sequencing the target nucleic acid in a second direction to obtain a second sequence signal information, wherein sequencing in the second direction includes extending the second primer in the second direction;

aligning at least a portion of the first and second sequence signal information;

determining a degree of agreement between the first and second sequence signal information for a location along a polynucleotide;

determining a weighted average signal for the location based on the first and second sequence signal information; and determining a base call and quality value for the location based on the weighted average signal and the degree of agreement.

2. The method of claim 1, wherein the first and second sequence signal information comprise first and second flow space information.

3. The method of claim 2, wherein the determining a weighted average signal applies respective weights to respective values of the first and second sequence signal information for the location, wherein the respective weights are based on respective accuracies of the first and second sequence signal information for the location.

* * * * *